United States Patent [19]

Cross et al.

[11] Patent Number: 5,009,647
[45] Date of Patent: Apr. 23, 1991

[54] WATER CLOSET DISPOSABLE OSTOMY BAGS AND MATERIALS

[75] Inventors: David E. Cross, Rustington; Kenneth J. Brooks, Lancing; Neil A. Whiteside, Worthing, all of England

[73] Assignee: Smiths Industries Public Limited Company, London, United Kingdom

[21] Appl. No.: 474,664

[22] Filed: Feb. 6, 1990

Related U.S. Application Data

[63] Continuation of Ser. No. 147,425, Jan. 25, 1988, abandoned.

[30] Foreign Application Priority Data

Feb. 19, 1987 [GB] United Kingdom ............... 8703874

[51] Int. Cl.$^5$ .............................................. A61F 5/44
[52] U.S. Cl. ........................................ 604/332; 383/1; 383/113
[58] Field of Search ................. 604/317, 332–345; 383/1, 109, 113, 114, 116, 908

[56] References Cited

U.S. PATENT DOCUMENTS

| | | | |
|---|---|---|---|
| 3,089,493 | 5/1963 | Galindo | 604/344 |
| 3,221,742 | 12/1965 | Orowan | 604/339 |
| 3,690,320 | 9/1972 | Riely | 604/333 |
| 3,934,587 | 1/1976 | Gordon | 604/364 |
| 4,620,999 | 11/1986 | Holmes | 428/35 |
| 4,653,640 | 3/1987 | Akao | 206/455 |
| 4,762,738 | 8/1988 | Keyes et al. | 604/332 |

FOREIGN PATENT DOCUMENTS

| | | | |
|---|---|---|---|
| 1561872 | 3/1980 | United Kingdom . | |
| 1562855 | 3/1980 | United Kingdom . | |
| 2029764 | 3/1980 | United Kingdom . | |
| 2083762 | 3/1982 | United Kingdom | 604/332 |
| 2123340 | 2/1984 | United Kingdom . | |
| 2143173 | 2/1985 | United Kingdom . | |
| 2149347 | 6/1985 | United Kingdom . | |

*Primary Examiner*—C. Fred Rosenbaum
*Assistant Examiner*—Corrine Maglione
*Attorney, Agent, or Firm*—Pollock, Vande Sande and Priddy

[57] ABSTRACT

A wc disposable ostomy bag has a wall formed from an inner layer of polyethylene and an outer layer of polyvinyl alcohol. Two flexible layers of aluminum are located between the inner and outer layers to reduce odor transmission through the wall. The material of the walls may be formed by vapor depositing the aluminum layers on respective faces of the inner and outer layers and then laminating the inner and outer layers together with the aluminum layers facing one another. Alternatively, both aluminum layers may be deposited on the same one of the inner or outer layers with a thin non-metallic layer between them to prevent the aluminum layers having common grain boundaries.

4 Claims, 3 Drawing Sheets and MATERIALS

This application is a continuation of Ser. No. 147,425 filed on Jan. 25, 1988, abandoned.

BACKGROUND OF THE INVENTION

This invention relates to ostomy bags, to materials for making such bags, and to methods of making such materials.

Ostomy bags are used for various purposes, for collecting material discharged from colostomies, ileostomies and urostomies. These bags are generally of a lightweight, flexible plastics material and may be disposable by flushing in a w.c.

In order to prevent odor transmission through the wall of previous bags it has been the practice to use a layer of PVDC or similar material as an odor barrier. In some circumstances, however, such as in w.c. disposable bags this may not be suitable, and odor release from the bag may be a problem leading to embarrassment by the user.

BRIEF SUMMARY OF THE INVENTION

It is an object of the present invention to provide an ostomy bag, a material for making such a bag, with reduced odor transmission; and a method of making such material.

According to one aspect of the present invention there is provided an ostomy bag having a wall thereof comprising an inner layer, an outer layer and a flexible metallic layer intermediate said inner and outer layer that is effective to reduce odor transmission through the wall.

The wall may include at least two flexible metallic layers intermediate the inner and outer layers. The wall may include a non-metallic layer intermediate the two metallic layers. One metallic layer may be formed by depositing on the inner layer and the other metallic layer formed by depositing on the outer layer. The or each metallic layer is preferably formed by vapor deposition.

At least the inner layer may be of polyethylene and preferably both the inner and outer layers are of a plastics material. The or each metallic layer may be of aluminum.

The wall of the bag is preferably wc disposable, the outer layer being of polyvinyl alcohol. The bag may be of a material that is disposable in a wc on contact with a chemical additive, such as an alkali, introduced to the bag or wc pan.

According to another aspect of the present invention there is provided a material for forming the walls of an ostomy bag, the material comprising a first and second layer of flexible plastics material and a third layer of a flexible metallic material located intermediate the first and second layers to reduce odor transmission through the material.

The material preferably includes at least two flexible metallic layers intermediate the first and second layers of flexible plastics material. At least that layer forming the inner layer of the bag may be of polyethylene. The or each metallic layer is preferably of aluminum.

The material may be wc disposable, the outer layer of the bag being of polyvinly alcohol. The material may be disposable in a wc on contact with a chemical additive, such as an alkali, introduced to the bag or wc pan.

According to a further aspect of the present invention there is provided a method of making material for forming the walls of an ostomy bag comprising the steps of forming a flexible metallic layer on a face of both a first and second layer of a flexible plastics material and then laminating the first and second layers together with their metallic layers facing one another.

According to yet another aspect of the present invention there is provided a method of making material for forming the walls of an ostomy bag comprising the steps of forming a flexiable metallic layer on a first layer of flexible plastics material, forming a flexible non-metallic layer on the first metallic layer, forming a second flexible metallic layer on the non-metallic layer, and laminating a second layer of flexible plastics material to the first layer of plastics material with the first and second metallic layers intermediate the first and second layers of plastics material.

A w.c. disposable ostomy bag and a material for the bag, in accordance with the present invention will now be described, by way of example, with reference to the accompanying drawings.

BRIEF DISCRIPTION OF THE DRAWINGS

DETAILED DESCRIPTION

Figure 1:
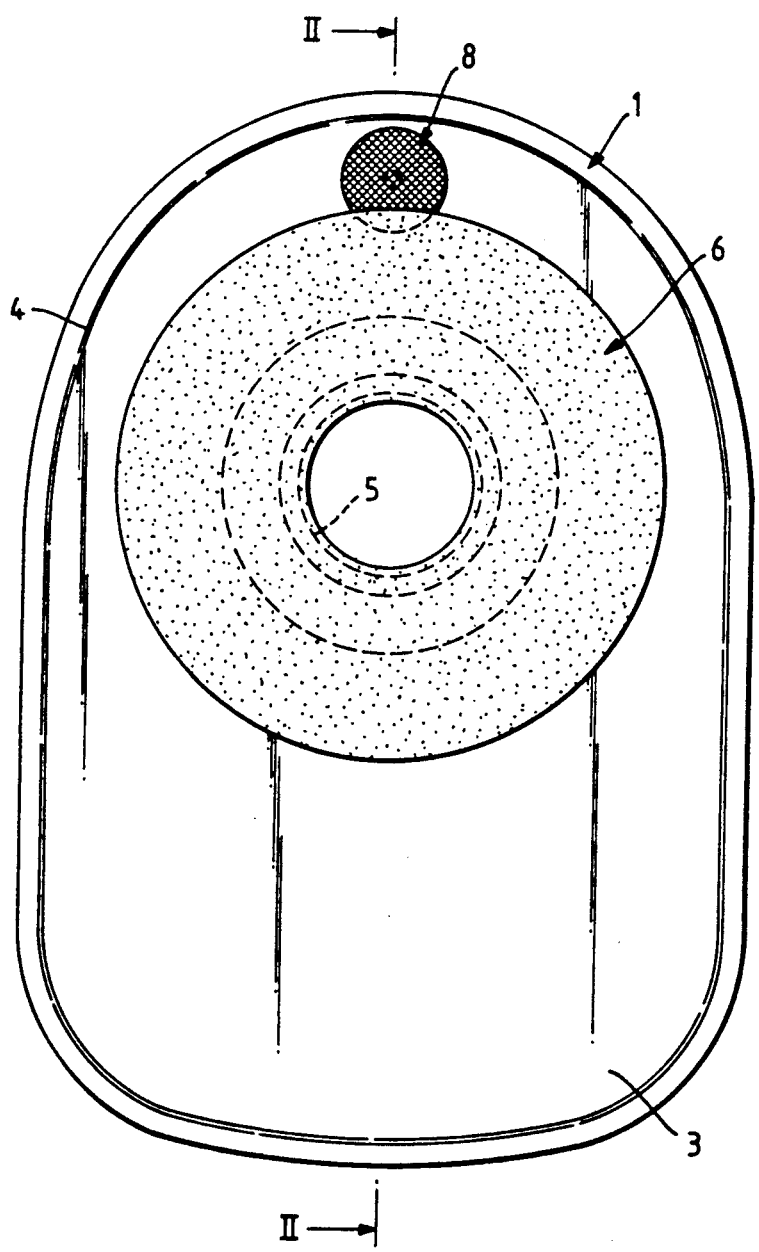
FIG. 1 is a plan view of the bag.
Figure 2:
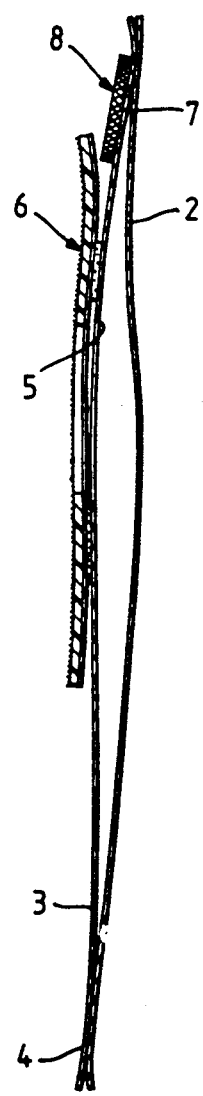
FIG. 2 is a sectional side elevation of the bag along the line II—II of FIG. 1.

With reference to FIGS. 1 and 2, the ostomy bag 1 is of conventional generally oblong shape and is formed from two walls 2 and 3 of the same flexible material that are joined together by welding around their edge 4 to form a sealed bag. An opening 5 is cut in one wall 3 towards its upper end and an annular adhesive flange 6 has one face secured to the wall 3 around the opening 5, the other face of the flange being used to secure the bag to the patient's skin around the stoma. A vent 7 with a flatus filter 8 is provided above the opening 5 in the wall 3.

Figure 3:
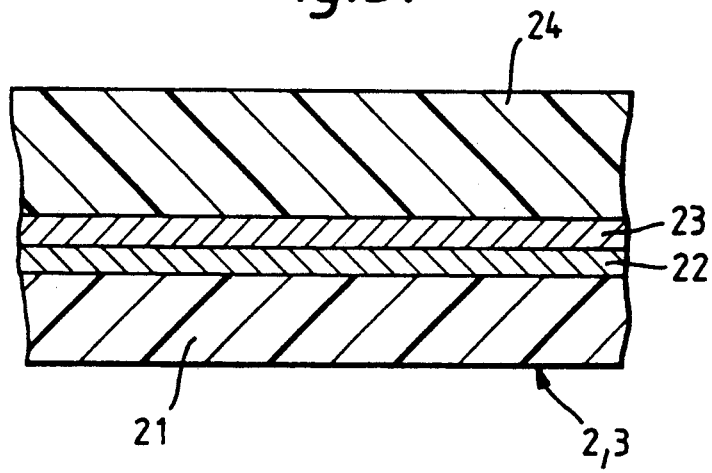
FIG. 3 is an enlarged sectional view through the wall of the bag.

The material from which the bag 1 is made is novel and is shown in FIG. 3, although the thicknesses of the different layers are not shown to scale. The material of both walls 2 and 3 comprises four layers: an inner layer 21, two intermediate metallic layers 22 and 23 and an outer layer 24.

The inner layer 21 is exposed on its surface, that is, to the contents of the bag 1, while the outer layer is exposed on the outer surface of the bag. The inner layer 21 is a thin, flexible layer of polyethylene. Other materials which are undamaged by the contents of the bag could be used for the inner layer. These could include materials which are broken down on contact with a chemical additive, such as an alkali, introduced to the bag or to the w.c. pan. Where an alkali is the chemical additive, the material could be carboxylated acrylic acid. In this respect, both the inner and outer layers could be of a material that is broken down on contact with a chemical additive.

The metallic layers 22 and 23 are both of aluminum, the inner one of the metallic layers 22 being deposited on the outer surface of the inner layer 21, whilst the outer one of the metallic layers 23 is deposited on the inner surface of the outer layer 24. Other metals could be used to provide the metallic layers 22 and 23.

The outer layer 24 provides the major part of the structural support of the bag and is formed from a material that will be broken up or dipersed by the action of liquid in a w.c. pan. In this respect, the outer layer 24 may be water-soluble, such as of polyvinyl alcohol, or of a material that is acted on by the combined effect of the water in a w.c. pan and a chemical additive introduced to the pan with the bag. For example, the material may be of the kind that is broken up by the action of an alkali introduced to the w.c. water. Other materials such as polyethylene or PVOH could alternatively be used. After the outer layer 24 has been broken up, the inner layer 21 is sufficiently thin so that it provides no obstacle to flushing of the wc, either by collapsing about the contents of the bag or by being torn up by water pressure and turbulence.

The outer layer 24 may comprise more than one layer. For example, it may comprise an inner layer of polyvinyl alcohol and an outer layer of an alkali soluble material. Alternatively, the outer layer may be of a soluble paper material. In some cases, it may be necessary to pre-coat the inner surface of the outer layer 24 with a different material in order to enable it to receive readily the metallic layer 23.

The two metallic layers 22 and 23 have been found significantly to reduce the transmission of odor from the bag. The inner layer 21 of polyethylene has relatively low odor barrier properties and the use of the intermediate metallic layers 22 and 23 has been found to enable an acceptable bag to be produced. While a single metallic layer does provide an improvement, the use of two or more layers produces a greater barrier effect than would be produced from a single layer of the same thickness. This is thought to be because any odor transmission occurs at the grain boundaries of the metal forming the layers and that, when several layers are used, this ensures that, in general, the grain boundaries do not align and form a complete path for transmission through the thickness of the layers. The thickness of the metallic layers is selected by experiment according to the nature and thickness of the inner and outer layers and the severity of odor problems, the combined thickness of the layers being sufficient to reduce odor transmission to acceptable limits. In general, the metallic layers will form an opaque or semi-transparent layer without being so thick as to reduce flexibility or incur high manufacturing costs.

Figure 4:
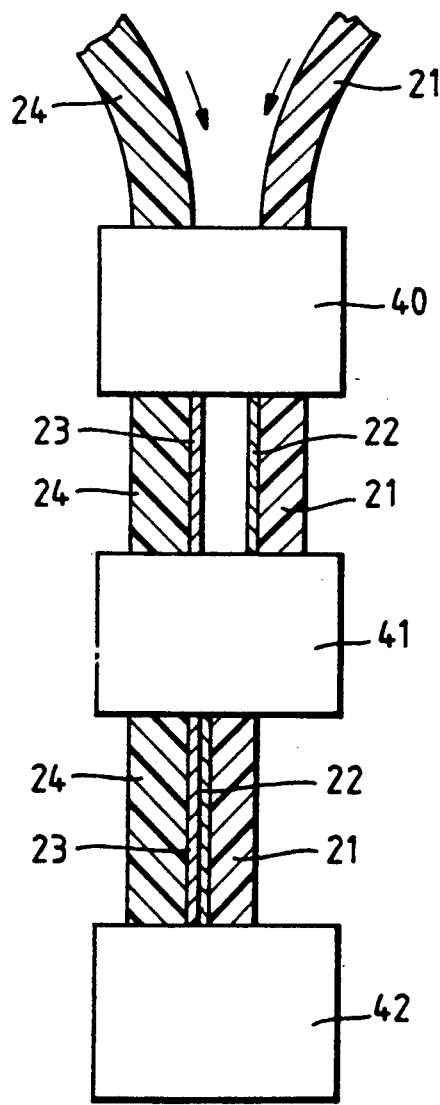
FIG. 4 illustrates the manufacture of the bag.

The bag 1 is made in the way illustrated in FIG. 4. The inner layer 21 of polyethylene and the outer layer 24 of the appropriate material are both fed into a conventional vapor deposition unit 40 in which a thin, flexible layer 22 and 23 of aluminum is deposited on one surface of each layer.

The metallized layers 21 and 24 are then supplied to a conventional laminating unit 41 in which the layers are laminated together with their metallized surfaces facing one another. The lamination is carried out by depositing a thin layer of adhesive on one or both the metallized surfaces and then bringing them together under heat and pressure.

The completed material is fed out of the laminating unit 41 to a conventional cutting and assembly unit 42 where the materials are cut to size and shape and joined together in the usual way, and with the flange 6, to produce the completed bag.

Figure 5:
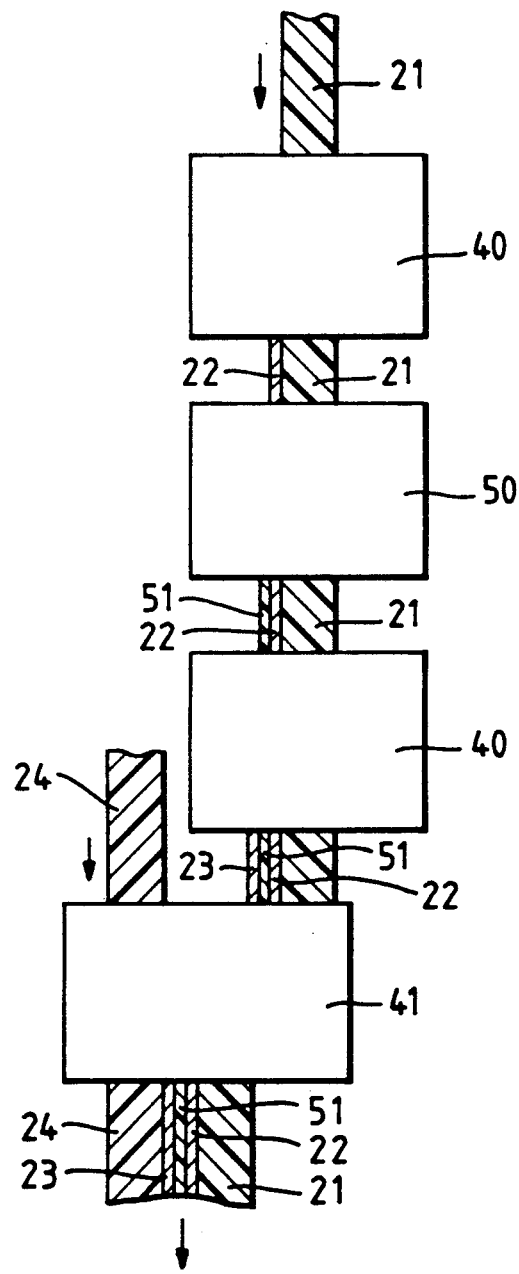
FIG. 5 illustrates the manufacture of an alternative bag.

An alternative method of making the bag and bag material in shown in FIG. 5. In this arrangement, only the inner layer 21 of polyethylene is fed into the vapor deposition unit 40 so that a thin, flexible layer 22 of aluminum is deposited on one surface. The metallized layer 21 is then fed to a coating unit 50 which forms a thin polymeric coating 51 on the exposed surface on the metal layer 22. This coated layer 21 is then fed again to the vapor deposition unit 40 where the second metallic layer 23 is deposited on top of the polymeric coating. The layer 21, after the formation of the two metallic layers 22 and 23, is supplied to the laminating unit 41 together with the outer layer 24 where it is laminated to the metallized surface of the inner layer 21. The lamination is carried out in the same way as in the process described with reference to FIG. 4 and the bags are also formed from the completed material in the same way.

This method enables the outer layer 24 to be of a material that is difficult to metallize. The non-metallic, polymeric coating 51 between the two metal layers 22 and 23 ensures that they do not become metallurgically integrated and therefore that the grain boundaries of the two layers are not aligned, thereby preventing odor penetration through the material.

It will be appreciated that various modifications are possible to the bag and that the invention also finds application to bags which are not w.c. disposable but which are formed from other materials and from materials with low odor barrier properties, such as polyethylene, EVA, polyurethane or PVC. The inner and outer layers can be of the same or different materials. The present invention may enable the use of materials which, although desirable from other aspects, have heretofore not been practical to use because of their low odor barrier properties.

The metallized internal layer of the bag material also has the added property of rendering the material opaque, which may be desirable in some circumstances, and of giving it a pleasing appearance.

What is claimed is:

1. An ostomy bag that is disposable in a w.c. by addition of an alkali to the bag or w.c., the bag comprising a flexible wall having an opening therein through which body waste material, in use, enters the bag and is contained thereby; said flexible wall comprising an inner layer disposed on an inner side of the bag, said inner layer being undamaged by the contents of the bag, and an outer layer disposed on an outer side of the bag, both of said inner and outer layers being of material that is broken up on contact with alkali, said material including carboxylated acrylic acid; at least two separately vapor diposited layers of aluminum intermediate said inner and outer layers, the thickness of each aluminum layer by itself being insufficient to prevent odor transmission but said layers in combination being effective substantially to prevent odor transmission through said wall to an extent greater than would be produced by a single aluminum layer equal in thickness to the total thickness of the two aluminum layers, and the two layers of aluminum being exposed to attack by said alkali through said wall after break up of said inner or outer layer and being soluble in said alkali.

2. An ostomy bag according to claim 1 wherein one of said vapor deposited layers of aluminum is on said inner layer and another of said vapor deposited aluminum layers is on said outer layer.

3. An ostomy bag that is disposable in a w.c. by addition of an alkali to the bag or w.c., the bag comprising a flexible wall having an opening therein through which body waste material, in use, enters the bag and is contained thereby; said flexible wall comprising an inner layer disposed on an inner side of the bag, said inner layer being undamaged by the contents of the bag, and an outer layer disposed on an outer side of the bag, both said inner and outer layers being of carboxylated acrylic acid that is broken up on contact with alkali; at least one vapor deposited layer of aluminum intermediate said inner and outer layers, the thickness of the aluminum layer being such that the combination of said aluminum layer with said inner and outer layers in said wall is effective substantially to prevent odor transmission through said wall, said aluminum layer being exposed to attack by said alkali through said wall after break up of said inner or outer layer and being thin enough to be rapidly dissolved by said alkali and to allow the underlying layer to be attacked by the alkali.

4. The ostomy bag of claim 3 wherein said vapor deposited aluminum layer is flexible and so thin as to be semi-transparent.

* * * * *